United States Patent [19]
Rupinskas

[11] Patent Number: 4,704,109
[45] Date of Patent: * Nov. 3, 1987

[54] SURGICAL SPONGE
[75] Inventor: Vytautas Rupinskas, Quincy, Mass.
[73] Assignee: The Kendall Company, Boston, Mass.
[*] Notice: The portion of the term of this patent subsequent to Feb. 24, 2004 has been disclaimed.
[21] Appl. No.: 944,280
[22] Filed: Dec. 18, 1986

Related U.S. Application Data

[63] Continuation of Ser. No. 777,041, Sep. 17, 1985, abandoned, and a continuation-in-part of Ser. No. 525,528, Aug. 22, 1983, abandoned.

[51] Int. Cl.4 .......................................... A61F 13/16
[52] U.S. Cl. .................................................. 604/362

[58] Field of Search ............................ 604/362, 384

[56] References Cited

U.S. PATENT DOCUMENTS 4,515,594  5/1985  Pendergrass et al. .............. 604/384
4,645,499  2/1987  Rupinskas ........................... 604/362

Primary Examiner—John D. Yasko
Attorney, Agent, or Firm—Powell L. Sprunger

[57] ABSTRACT

A surgical sponge comprising, a sheet of absorbent material comprising entangled fibers. The sponge has an elongated radiopaque element in the sheet, with the fibers being fluidentangled about the element to retain it in place in the sheet.

6 Claims, 4 Drawing Figures

SURGICAL SPONGE

This is a continuation division of application Ser. No. 777,041, filed Sept. 17, 1985, now abandoned a continuation-in-part of application Ser. No. 525,528, filed Aug. 22, 1983, now abandoned.

BACKGROUND OF THE INVENTION

The present invention relates to absorbent articles, and more particularly to surgical sponges.

Surgical sponges are commonly used during surgical procedures to absorb body fluids of the patient both inside the incision and around the site of surgery. Sponges of this nature are usually made of an openmeshed absorbent fabric, such as woven cotton.

It is important, of course, that all of such sponges be removed from the patient's body after surgery is complete and before the incision has been closed. Accordingly, it is a standard procedure for the surgical team to carefully count the sponges to reduce the possibility that a sponge may be left in the patient.

In spite of such safety measures, sponges have been occasionally lost, particularly when an unexpected emergency disrupted the normal operative routine such as counting, which is subject to human error. When saturated by body fluids, such as blood, the sponges become significantly reduced in size and assume a color the same as body tissue, thus making visual detection of the sponges extremely difficult. As a result, it has been required to provide the sponges with a flexible insert which is opaque to X-rays. In case of a disputed or non-tallying sponge count in the operating room, or in case of unexpected or unexplainable post-operative discomfort on the part of the patient, a portable X-ray unit is brought to the patient and an X-ray exposure should reveal the presence or absence of a lost sponge. A nagative plate should be reassurance to the surgeon that he and his operative team have not left a sponge in the patient. However, the radiopaque elements have normally been loosely placed in the sponge, resulting in the possibility that the elements might fall out of the sponge, and become lost in the patient's body.

SUMMARY OF THE INVENTION

A principal feature of the present invention is the provision of a surgical sponge of simplified construction which prevents mishaps in reclaiming sponges from a patient's body.

The sponge of the present invention comprises, a sheet of absorbent material comprising entangled fibers. The sponge has an elongated radiopaque element in the sheet.

A feature of the invention is that the fibers are fluidentangled about the element.

Another feature of the invention is that the fluidentangled fibers retain the element in place in the sheet.

Yet another feature of the invention is that the element is retained in place without the necessity of bonding the element to the sheet thus preventing degradation of the element.

A further feature of the invention is the provision of a method for making the sponge of the present invention.

Further features will become more fully apparent in the following description of the embodiments of this invention and from the appended claims.

DESCRIPTION OF THE PREFERRED EMBODIMENTS

Figure 1:
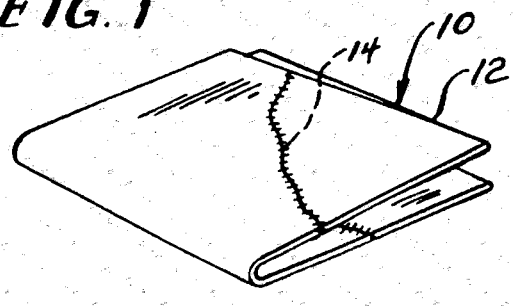
FIG. 1 is a perspective view of a surgical sponge of the present invention.
Figure 2:
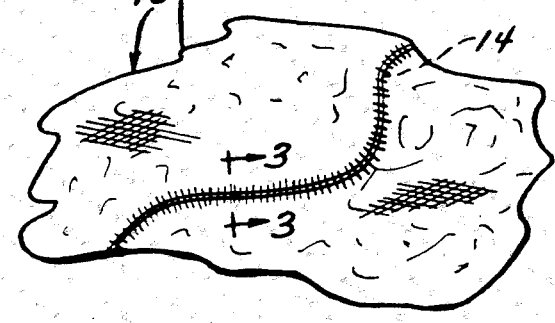
FIG. 2 is a fragmentary plan view of a portion of the sponge of the present invention.

Referring now to FIGS. 1 and 2, there is shown a surgical sponge generally designated 10 comprising a sheet 12 of absorbent material comprising entangled or fluidentangled fibers, and an elongated radiopaque element 14 embedded in the fibers in order to retain it in place. As shown in FIG. 1, in a preferred form, the sheet 12 is folded into a multi-ply configuration for use in and about the incision in a patient's body.

The fibers are randomly disposed in the sheet 12, and preferably comprise a hydrophilic material, such as rayon or cotton and may be either natural or synthetic. The radiopaque element 14 may comprise a thermoplastic vinyl material impregnated with barium sulfate to make the element 14 opaque to X-rays. The element 14 may be disposed in any suitable pattern or in a straight line in the sheet 12.

Figure 3:
FIG. 3 is a fragmentary sectional view taken substantially as indicated along the line 3—3 of FIG. 2.

With reference to FIG. 3, the fibers 16 of the sheet 12 are entangled with each other in order to provide the sheet 12 with strength and integrity. Also, as shown, the fibers 16 are entangled about both sides of the element 14 in order to hold the element 14 in place in the sheet 12, and prevent loss of the element 14 in a patient's body.

Figure 4:
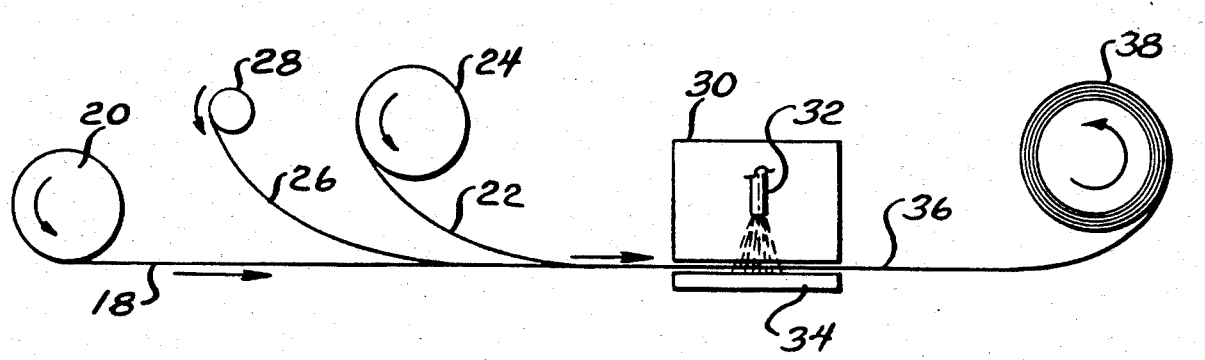
FIG. 4 is a diagrammatic view of a method or apparatus for making the sponge of the present invention.

A method of making the sponge 10 will be described in connection with FIG. 4. As shown, the apparatus or method has a first layer or card 18 comprising a mass of randomly disposed fibers which is unwound from a roll 20 and passed in the direction as indicated by the arrow. Also, the apparatus or method has a second layer or card 22 comprising a mass of randomly disposed fibers which is unwound from a roll 24 and passed in the direction as indicated by the arrow slightly above and adjacent to the first layer 18. The method or apparatus has an elongated radiopaque element 26 of the type previously described which is unwound from a roll 28, and which is placed intermediate the first layer 18 and second layer 22 and passed in the direction passed by the first and second layers 18 and 22. The first layer 18, second layer 22, and element 26 are passed through a fluidentangling station 30 where water, air, or steam jets 32 force water, air, or steam against the fibers of the first and second layers 18 and 22, such that the fibers of the first and second layers 18 and 22 are fluidentangled together and are fluidentangled about the element 26 in order to retain it in place between the fluidentangled fibers. The water passing through the layers 18 and 22 then passes through a screen 34 for appropriate disposal. The resulting web 36 from the station 30 containing the locked-in element 26 passes from the station 30, and may be wound into a roll 38. The roll 38 may be subsequently slitted to an appropriate shape, and the slitted fabric may be folded into a multi-ply configuration to form the surgical sponge, as shown in FIG. 1.

Thus, in accordance with the present invention, a sheet 12 of nonwoven material comprising fluidentangled fibers is formed, with the fibers being entangled about a radiopaque element 14 in order to retain the element 14 in place in the sheet 12. In this manner, the element 14 is prevented from falling out of the sponge 10 when used in the patient's body, thus preventing loss of the element 14 in the patient's body.

The foregoing detailed description is given for clearness of understanding only, and no unnecessary limitations should be understood therefrom, as modifications will be obvious to those skilled in the art.

I claim:

1. A surgical sponge, comprising,
   a sheet of absorbent material comprising entangled fibers; and
   an elongated radiopaque element in the sheet, said fibers being fluidentanged about the element such that the element is embedded in the sheet to retain it in place in the sheet.

2. The sponge of claim 1 wherein the sheet is folded into a multi-ply configuration.

3. The sponge of claim 1 wherein said fibers are hydrophilic.

4. The sponge of claim 3 wherein said fibers comprise cotton.

5. The sponge of claim 3 wherein said fibers comprise rayon.

6. A method of making a surgical sponge, comprising the steps of:
   passing a first layer of a mass of fibers;
   passing a second layer of a mass of fibers adjacent the first layer;
   placing an elongated radiopaque element intermediate the first and second layers; and
   fluidentangling the fibers of the first and second layers together and about said element to form a sheet of entangled fibers with the element embedded in the sheet.

* * * * *